US010827927B2

(12) United States Patent
Boss et al.

(10) Patent No.: US 10,827,927 B2
(45) Date of Patent: Nov. 10, 2020

(54) AVOIDANCE OF COGNITIVE IMPAIRMENT EVENTS

(71) Applicant: International Business Machines Corporation, Armonk, NY (US)

(72) Inventors: Gregory J. Boss, Saginaw, MI (US); Jill S. Dhillon, Houston, TX (US); Rick A. Hamilton, II, Charlottesville, VA (US); James R. Kozloski, New Fairfield, CT (US)

(73) Assignee: International Business Machines Corporation, Armonk, NY (US)

( * ) Notice: Subject to any disclaimer, the term of this patent is extended or adjusted under 35 U.S.C. 154(b) by 268 days.

(21) Appl. No.: 15/848,092

(22) Filed: Dec. 20, 2017

(65) Prior Publication Data

US 2018/0110412 A1    Apr. 26, 2018

Related U.S. Application Data

(63) Continuation of application No. 14/328,349, filed on Jul. 10, 2014, now abandoned.

(51) Int. Cl.
*A61B 5/00* (2006.01)
*G16H 40/67* (2018.01)
(Continued)

(52) U.S. Cl.
CPC ........ *A61B 5/0022* (2013.01); *A61B 5/02055* (2013.01); *A61B 5/6803* (2013.01);
(Continued)

(58) Field of Classification Search
CPC ..... A61B 5/486; A61B 5/6803; A61B 5/7246; A61B 5/725; A61B 5/746; A61B 5/7282; A61B 5/7275; A61B 5/11
See application file for complete search history.

(56) References Cited

U.S. PATENT DOCUMENTS 5,621,922 A * 4/1997 Rush, III ............... G01P 15/18
2/422
7,547,279 B2   6/2009 Kim
(Continued)

FOREIGN PATENT DOCUMENTS

EP      2660745 A2   11/2013
WO    2012025622 A2   3/2012

OTHER PUBLICATIONS

U.S. Appl. No. 14/299,698 Non-Final Office Action dated Jun. 28, 2018.

(Continued)

*Primary Examiner* — Nathan J Jenness
(74) *Attorney, Agent, or Firm* — Law Office of Jim Boice

(57) ABSTRACT

A method controls an alert indicator on a helmet. A physiological sensor and an accelerometer sensor in the helmet monitor a wearer of the helmet. A human observer subjectively detects that the wearer of the helmet is showing signs of an impaired cognitive state, and sends a signal/marker that marks a point in the sensor readings that the impaired cognitive state manifested itself. A subsequent series of sensor readings from the physiological and accelerometer sensors are taken at a later time. If this subsequent series of sensor readings matches the earlier sensor readings up to the point that the human observer subjectively detected the helmet wearer's impaired cognitive state, then an alert indicator is activated on the helmet, warning the wearer of the helmet of an impending recurrence of the impaired cognitive state for the wearer of the helmet.

20 Claims, 7 Drawing Sheets

(51) Int. Cl.
*A61B 5/11* (2006.01)
*A61B 5/16* (2006.01)
*A61B 5/0205* (2006.01)
*G06F 19/00* (2018.01)

(52) U.S. Cl.
CPC ............ *A61B 5/7282* (2013.01); *A61B 5/746* (2013.01); *G06F 19/00* (2013.01); *G16H 40/67* (2018.01); *A61B 5/112* (2013.01); *A61B 5/165* (2013.01); *A61B 5/4803* (2013.01); *A61B 5/725* (2013.01); *A61B 5/7275* (2013.01); *A61B 5/749* (2013.01); *A61B 2560/0242* (2013.01)

(56) References Cited

U.S. PATENT DOCUMENTS

| | | | |
|---|---|---|---|
| 7,653,605 | B1 | 1/2010 | Jackson |
| 7,788,208 | B2 | 8/2010 | Kobayashi et al. |
| 7,874,983 | B2 | 1/2011 | Zancho et al. |
| 8,108,033 | B2 | 1/2012 | Drew et al. |
| 8,412,665 | B2 | 4/2013 | Wang et al. |
| 8,621,673 | B1* | 1/2014 | Pietrantonio ........ A61B 5/4076 2/410 |
| 2001/0031930 | A1 | 10/2001 | Roizen et al. |
| 2005/0277813 | A1 | 12/2005 | Katz et al. |
| 2009/0002178 | A1 | 1/2009 | Guday et al. |
| 2010/0217097 | A1 | 8/2010 | Chen et al. |
| 2010/0324427 | A1 | 12/2010 | Devot et al. |
| 2011/0184663 | A1* | 7/2011 | Mack ........................ G01L 1/26 702/41 |
| 2011/0263946 | A1 | 10/2011 | El Kaliouby et al. |
| 2011/0301436 | A1 | 12/2011 | Teixeira |
| 2012/0029311 | A1 | 2/2012 | Raptis et al. |
| 2012/0143526 | A1* | 6/2012 | Benzel ................. A61B 5/7278 702/42 |
| 2012/0289789 | A1 | 11/2012 | Jain et al. |
| 2013/0060168 | A1* | 3/2013 | Chu ..................... A61B 5/6803 600/595 |
| 2013/0262182 | A1 | 10/2013 | Kodra et al. |
| 2013/0271602 | A1* | 10/2013 | Bentley .............. G06K 9/00342 348/143 |
| 2014/0073993 | A1* | 3/2014 | Poellabauer ......... A61B 5/4064 600/586 |
| 2014/0223990 | A1* | 8/2014 | Reuben ..................... G01L 1/00 73/12.04 |
| 2014/0266752 | A1* | 9/2014 | John ................... G08B 21/0461 340/665 |
| 2015/0040685 | A1* | 2/2015 | Nicholson ............ A61B 5/4064 73/862.51 |
| 2015/0206053 | A1 | 7/2015 | Hayden |
| 2015/0226621 | A1 | 8/2015 | Zhu et al. |
| 2015/0305426 | A1 | 10/2015 | Lee et al. |
| 2016/0018278 | A1* | 1/2016 | Jeter, II ................. G01L 5/0052 340/665 |

OTHER PUBLICATIONS

U.S. Appl. No. 14/299,698—Final Office Action dated Mar. 25, 2019.
U.S. Appl. No. 14/299,698 Final Office Action dated Jun. 8, 2017.
U.S. Appl. No. 14/299,698 Non-Final Office Action dated Jul. 14, 2016.
A.A. Abdullah, et al., "Design and Development of an Emotional Stress Indicator (ESI) Kit", IEEE, IEEE Conference on Sustainable Utilization and Development in Engineering and Technology (Student), 2012, Kuala Lumpur, pp. 253-257 (Abstract Only).
Fitbit, Inc., "Make Fitness a Lifestyle With Flex (TM)", Fitbit, Inc., <www.fitbit.com/flex>, Retrieved June 6, 2014, pp. 1-7.
List of IBM Patents or Patent Applications Treated as Related, Dec. 20, 2017, pp. 1-2.
B. Sauser, "A Helmet That Detects Hard Hits", MIT Technology Review, Sep. 10, 2007, pp. 1-2.
U.S. Appl. No. 14/328,349 Non-Final Office Action dated Aug. 11, 2016.
U.S. Appl. No. 14/328,349 Final Office Action dated Jul. 7, 2017.

\* cited by examiner

AVOIDANCE OF COGNITIVE IMPAIRMENT EVENTS

BACKGROUND

The present disclosure relates to the field of computers, and specifically to the use of computers in evaluating cognitive states. Still more particularly, the present disclosure relates to assisting a person in avoiding an impairment event associated with one or more cognitive states.

A person's cognitive state is also known as a person's "state of mind". This state of mind may be normal (e.g., interested, sleepy, asleep, alert, bored, curious, doubtful, etc.), or it may be indicative of some type of pathology (e.g., amnesia, confusion, panic, etc.). Often, such states of mind will manifest themselves measurably before a person (subjectively) realizes that he/she is entering such a state of mind.

SUMMARY

A method controls an alert indicator on a helmet. A physiological sensor in the helmet detects a biological state of a wearer of the helmet. An accelerometer sensor in the helmet detects a change in velocity of the helmet. One or more processors store a first set of time-dependent sensor readings from the physiological sensor and the accelerometer sensor into a first buffer in the helmet. A receiver in the helmet receives a first cognitive impairment state signal. The first cognitive impairment state signal is sent by a human observer of the wearer of the helmet in response to the human observer subjectively observing an impairment to a cognitive state of the wearer of the helmet. One or more processors in the helmet insert a cognitive impairment state marker in the first buffer in the helmet, where the cognitive impairment state marker is set at a position that is associated with the receiver in the helmet receiving the first cognitive impairment state signal. The processor(s) in the helmet load a second set of time-dependent sensor readings from the physiological sensor and the accelerometer sensor into a second buffer in the helmet, where the second set of time-dependent sensor readings are generated after the receiver in the helmet receives the first cognitive impairment state signal. The processor(s) in the helmet compare the first set of time-dependent sensor readings up to the cognitive impairment state marker to the second set of time-dependent sensor readings, and determine that the first set of time-dependent sensor readings up to the cognitive impairment state matches the second set of time-dependent sensor readings. In response to determining that the first set of time-dependent sensor readings up to the cognitive impairment state matches the second set of time-dependent sensor readings, the processor(s) in the helmet activate an alert indicator in the helmet, where the alert indicator is a physical device that warns the wearer of the helmet of an impending recurrence of an impaired cognitive state for the wearer of the helmet.

In one or more embodiments of the present invention, the present invention is implemented as a computer program product and/or in a system.

DETAILED DESCRIPTION

Figure 1:
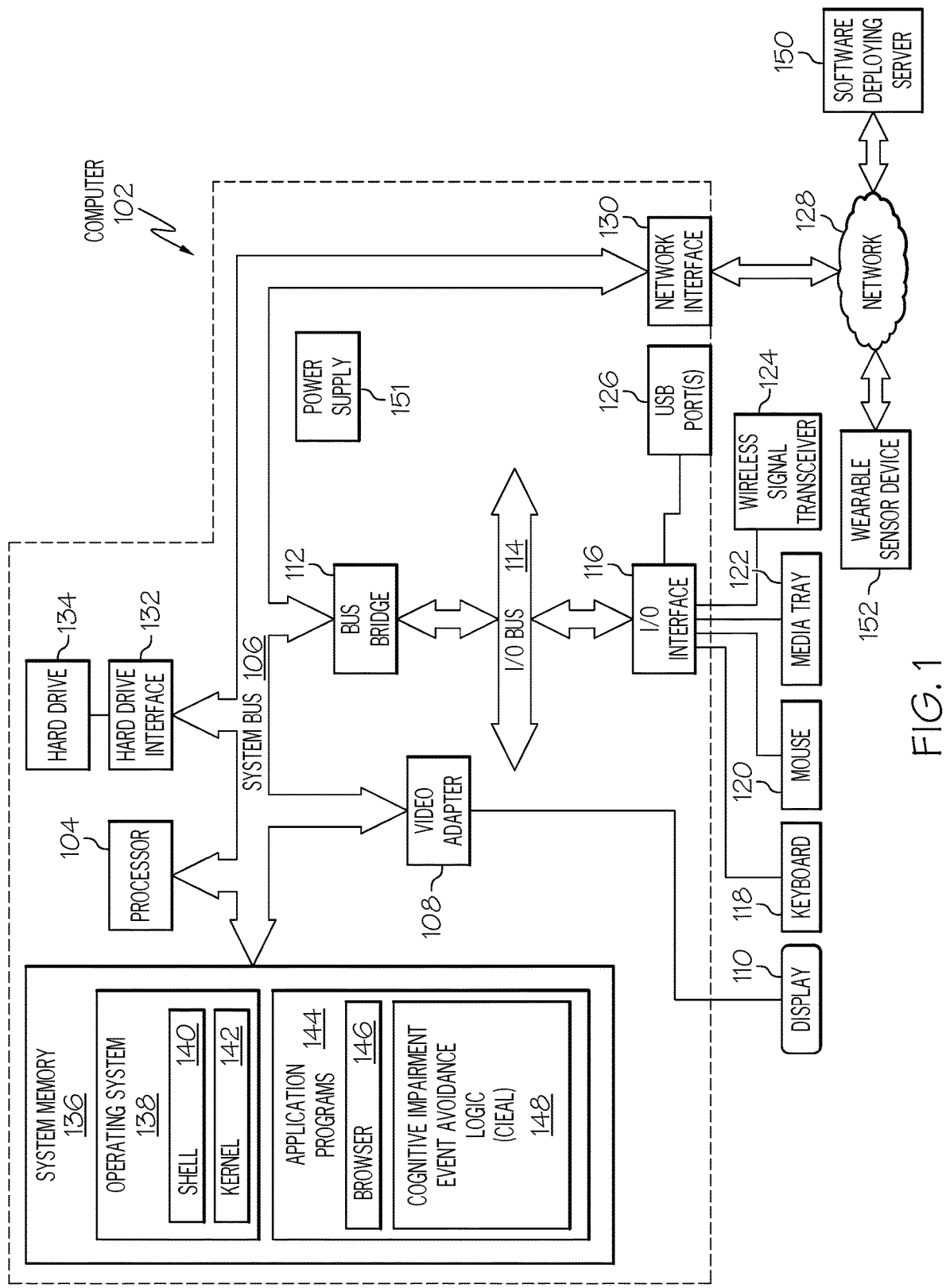
FIG. 1 depicts an exemplary system and network in which the present disclosure may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Note that some or all of the exemplary architecture, including both depicted hardware and software, shown for and within computer 102 may be utilized by software deploying server 150 and/or a wearable sensor device 152, as well as impairment signal transmitters 506 shown in FIG. 5 and FIG. 6, and/or monitoring system 602 shown in FIG. 6.

Exemplary computer 102 includes a processor 104 that is coupled to a system bus 106. Processor 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a wireless signal transceiver 124 (e.g., a near field radio frequency transceiver, a Wi-Fi transceiver, etc.), and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150, using a network interface 130. Network interface 130 is a hardware network interface, such as a network interface card (NIC), etc. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (as well as software deploying server 150's system memory) also include a Cognitive Impairment Event Avoidance Logic (CIEAL) 148. CIEAL 148 includes code for implementing the processes described below, including those described in FIGS. 2-7. In one embodiment, computer 102 is able to download CIEAL 148 from software deploying server 150, including in an on-demand basis, wherein the code in CIEAL 148 is not downloaded until needed for execution. Note further that, in one embodiment of the present invention, software deploying server 150 performs all of the functions associated with the present invention (including execution of CIEAL 148), thus freeing computer 102 from having to use its own internal computing resources to execute CIEAL 148.

Note that computer 102 is connected to a power supply 151 used to power various components within computer 102 and/or connected components (e.g., elements 110, 118, 126, 128, etc.) In various embodiments, power supply 151 may be a solar cell, a battery (rechargeable or non-rechargeable), a public utility power grid that is accessible via a wall socket, a local limited supply source (e.g., a local fuel-powered generator), etc.

Note that the hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

As a high-level overview of one or more embodiments of the present invention, the present invention takes three steps. The first step is to capture sensor readings that describe circumstantial environments of a wearer of a sensor device, and to store them in a buffer. Thereafter (the second step), an observer (in one or more embodiments a human observer) of the wearer of the sensor device, in response to observing an impairment to the cognitive state of the wearer of the sensor device, takes some action, which results in a marker being placed in the buffer. Thereafter (the third step), if the wearer of the sensor device repeats actions that lead to sensor readings matching those found in the first buffer, then an alert is given to the wearer to take evasive actions to avoid the effects of again experiencing the impaired cognitive state that resulted from the circumstantial environments captured in the first step.

Figure 2:
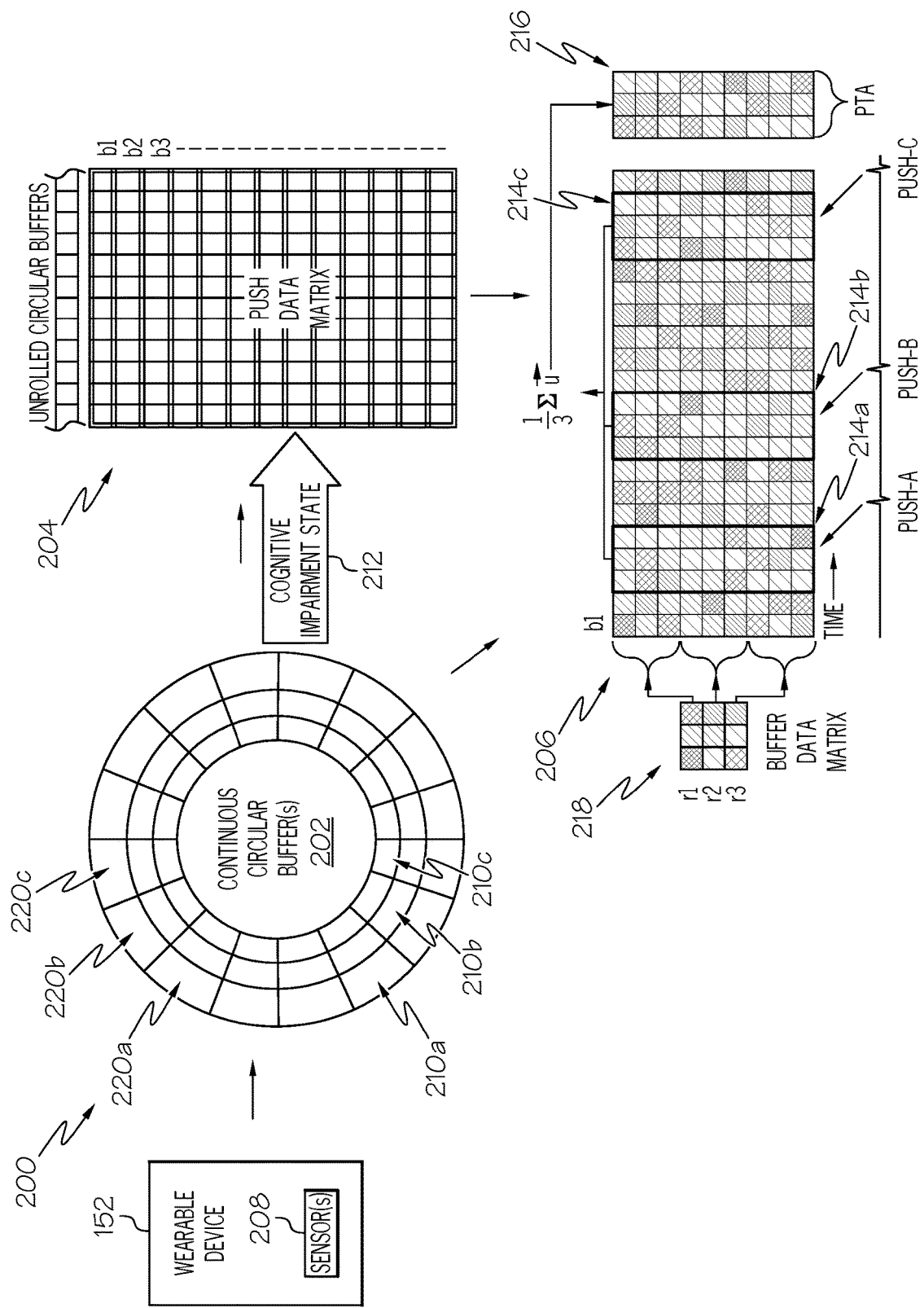
FIG. 2 illustrates an exemplary Impaired Cognitive State Predictor (ICSP) architecture in accordance with one or more embodiments of the present invention.

With reference now to FIG. 2, an exemplary Impaired Cognitive State Predictor (ICSP) architecture 200 is presented in accordance with one or more embodiments of the present invention. Note that the ICSP architecture 200 and data generated by the ICSP architecture is secret. That is, predictions of current or future cognitive states are presented only to the user that generated the sensor readings described herein and/or experiences the specific cognitive state that follows these sensor readings. Only with the express approval of the user (i.e., wearer of the wearable sensor device described herein) will such readings/states be shared with others.

Note that in one embodiment the ICSP architecture 200 also includes multiple components found in FIG. 1 (e.g., computer 102, wearable sensor device 152, etc.). Furthermore, in one embodiment, the continuous circular buffer(s) 202, the push data matrix 204, and/or the accumulation data matrix 206 shown in FIG. 2 and/or components shown in FIG. 1 are all within the wearable sensor device 152. In one or more other embodiments, the continuous circular buffer(s) 202 are within the wearable sensor device, but the push data matrix 204 and/or accumulation data matrix 206 are stored in a hardware storage device (e.g., system memory 136 and/or hard drive 134 shown in FIG. 1) on a remote computer, such as computer 102 shown in FIG. 1.

Wearable sensor device 152 includes one or more sensor(s) 208. In one embodiment, each of the sensor(s) 208 are "smart sensors", that include processing logic that is able to detect, record, and quantify what is being sensed. That is, each of the sensor(s) 208 is 1) able to detect a particular physical event (heat, noise, biometrics, etc.); 2) quantify the level of that particular physical event (e.g., how high the heat is, what the duration/intensity of the noise is, what the specific readings of the biometric is, etc.); 3) convert that level into a digital value; and/or 4) send that digital value to the continuous circular buffer(s) 202. In one embodiment, these functions are performed by dedicated hardware logic, which takes digital readings from the sensors, compares the digital readings to known ranges in order to establish the digital value, and then transmits (e.g., by a wireless digital signal transmitter) the digital value to the continuous circular buffer(s) 202, which then (responsive to a "push" signal) send the stored digital values from the continuous circular buffer(s) 202 to a local matrix within the wearable sensor device 152 or to a remote matrix in a remote computer (e.g., computer 102 shown in FIG. 1). In either embodiment, the system can use a near field network to send the digital value to a local storage within the wearable sensor device 152, or to a remote device, such as a smart phone held by the user, or to a server on a cloud, etc. (e.g., using a Wi-Fi signal).

Note that in one or more embodiments of the present invention, data stored in the continuous circular buffer(s) 202 is time-based. For example, data found in buffer cell 220*a* is received before data that is received and stored in buffer cell 220*b*, which stores data that is received before data that is received and stored in buffer cell 220*c*, etc. Thus, the data stored in continuous circular buffer(s) 202 (and thus the push data matrix 204) is "time-based".

In one embodiment, sensor(s) 208 include physiological sensors, which are defined as sensors that are able to detect physiological states of a person. In one embodiment, these sensors are attached to the person via the wearable sensor device 152. Example of such sensors include, but are not limited to, a heart monitor, a blood pressure cuff/monitor (sphygmomanometer), a galvanic skin conductance monitor, an electrocardiography (ECG) device, an electroencephalography (EEG) device, etc. That is, in one embodiment, the sensor(s) 208 are biometric sensors that measure physiological functions, of the wearer, which are not musculoskeletal.

In one embodiment, sensor(s) 208 detect and/or measure musculoskeletal bodily acts of the user, such as facial expressions (e.g., smiles, frowns, furrowed brows, etc.), body movements (e.g., walking gait, limps, stride length, stride speed, etc.), etc. Facial expressions may be detected by muscle movement sensors on eyeglasses, cameras on "smart glasses", etc. Body movements may be detected by motion detectors, stride counters, strain gauges in clothing, etc.

In one embodiment, sensor(s) 208 include speech content analyzers. In this embodiment, the sensor(s) 208 includes a speech-to-text converter, which then examines the text for certain keywords, speech pattern, etc. That is, the speech-to-text converter converts spoken words into written text, which can then be examined in order to identify certain predefined keywords, speech pattern, etc. The presence (or absence) of such keywords, speech pattern, etc. is then used by logic (e.g. CIEAL 148 in FIG. 1) to ascertain the nature of the speech, which may lead to a warning of a future cognitive impairment state of the user (as described herein).

In one embodiment, sensor(s) 208 include speech content analyzers. In this embodiment, the sensor(s) 208 includes a speech-to-text converter, which then examines the text for certain features. These features may include the construction of graphs representing structural elements of speech based on a number of alternatives, such as syntactic value (article, noun, verb, adjective, etc.), or lexical root (run/ran/running) for the nodes of the graph, and text proximity for the edges of the graph. Graph features such as link degree, clustering, loop density, centrality, etc., representing speech topological structure are also therefore included. Similarly, semantic vectors may be extracted from the text as features, using systems such as that provided by a Latent Semantic Analysis, WordNet, etc. These methods allow the computation of a distance between words and specific concepts (e.g. introspection, anxiety, depression), such that the text can be transformed into features representing a field of distances to a concept, a field of fields of distances to the entire lexicon, or a field of distances to other texts including books, essays, chapters and textbooks. The syntactic and semantic features may then be combined either as a "bag of features" or as integrated fields, such as the Potts model. Similarly, locally embedded graphs may be constructed, so that a trajectory in a high-dimensional feature space is computed for each text. This trajectory is used as a measure of coherence of the speech, as well as a measure of distance between speech trajectories using methods such as Dynamic Time Warping.

In one embodiment, sensor(s) 208 include speech inflection analyzers. In this embodiment, the sensor(s) 208 compare voice patterns with known voice patterns (pitch, timing, tremor, etc.) of the user, in order to identify certain emotions such as stress, relaxation, alertness, sleepiness, and other cognitive states. The presence (or absence) of such voice patterns is then used by logic (e.g. CIEAL 148 in FIG. 1) to ascertain the current emotional state of the user, which may lead to a warning of a future cognitive impairment state of the user (as described herein).

In one embodiment, sensor(s) 208 include environmental sensors, such as an air thermometer, a microphone, a barometer, a light sensor, a moisture sensor, etc. In this embodiment, sensor(s) 208 are able to detect ambient (within the proximity of the user) environmental conditions, such as rain, various light levels, sound levels, air pressure, sound (e.g., noise, music, spoken words, etc.), etc.

In one embodiment, sensor(s) 208 include accelerometers, which measure acceleration and/or deceleration forces as an object accelerates (i.e., increases speed) and/or decelerates (i.e., slows down and/or stops). These acceleration/deceleration forces may be abrupt, particularly the deceleration forces that occur when a moving object strikes another object, which may be fixed, moving in a direction opposite that of the first object, or is moving in the same direction as the first object but at a slower speed.

As described herein, values stored in the continuous circular buffer(s) 202 are sent to the push data matrix 204 in response to a "push" event. In one embodiment, the "push" event occurs in response to an observer observing a wearer of the wearable sensor device 152 exhibiting an impaired cognitive state. That is, as soon as the observer "feels" (i.e., subjectively determines) that the wearer is in a particular impaired cognitive state (e.g., is boring, is unfocused, is disoriented, etc.), then the observer issues a "push" command, causing the contents of the continuous circular buffer(s) 202 to be loaded into the push data matrix 204. Note that in one or more embodiments of the present invention, the actions taken by the observer are based on the observer's subjective impressions, which are not based on clinical evidence. That is, the observations are not on unimpeachable scientific evidence of a particular pathology (e.g., an MRI that clearly shows damage to a cognition component of the brain), but rather are the subjective observations of the observer. Thus, one observer may view the wearer (person who is wearing the wearable sensor device 152) as being "fascinating" or "alert", while another observer may view the same wearer as being "boring" or "disoriented". Thus, the observers' observations are purely subjective in this embodiment, and are not directly correlated to any scientific/clinical facts supporting an impression of a specific cognitive impairment state.

Thus, in one or more embodiments of the present invention, sensor readings from sensor(s) 208 are buffered in the continuous circular buffer(s) 202. Continuous circular buffer(s) 202 are buffers that allow data to be stored in any location/cell within the buffer. Unlike a linear buffer (such as a First In First Out—FIFO buffer), a circular buffer allows "stale" data to be replaced with "fresh" data without shifting the location of existing data in other cells within the buffer. In one embodiment, continuous circular buffer(s) 202 is composed of multiple circular buffers 210a-210c (where "c" is an integer). In one embodiment, each of the circular buffers 210a-210c is devoted to storing readings from a specific sensor from sensor(s) 208.

For example, assume that circular buffer 210a is devoted to storing readings from a sensor 208 that measures a heart rate of the user. When data from circular buffer 210a is sent to push data matrix 204, it is stored in the unrolled buffer shown as b1. Assume further that circular buffer 210b is devoted to storing readings from a sensor 208 that measures an ambient light level where the user is located. When data from circular buffer 210b is sent to push data matrix 204, it is stored in the unrolled buffer shown as b2. Assume further that circular buffer 210c is devoted to storing readings from a sensor 208 that measures speech patterns of the user. When data from circular buffer 210c is sent to push data matrix 204, it is stored in the unrolled buffer shown as b3. Thus, readings from a particular sensor are stored in a particular circular buffer as well as a particular unrolled (linear) buffer in a buffer matrix.

Note that while the present disclosure presents continuous circular buffer(s) 202 as a single circle, other circular buffers having multiple interlocking circular buffers are contemplated as being within the scope of the present invention.

As described herein, data is sent from the continuous circular buffer(s) 202 to the push data matrix 204 in response to a "push" being initiated by an observer of the wearer of the wearable sensor device 152 observing a particular impaired cognitive state of the wearer. Note that in one embodiment, these observations are purely subjective. That is, the perception of a particular impaired cognitive state is subjective and unique to that observer. For example, one observer may determine that the wearer of the wearable sensor device 152 is experience the cognitive state of "lucid and interesting" when sensor(s) 208 detect a particular pattern of conditions (physiological, temporal, environmental, etc.). However, another observer may determine that the wearer of the wearable sensor device 152 is being "disorganized and boring" when sensor(s) 208 detect this same particular pattern of conditions for this same wearer. Thus, each observer may respond differently to the wearer when the same set/pattern of conditions occurs. In order to address this subjective variation among multiple observers, in one embodiment a smoothing function is used to "smooth out" the observations from the observers of the wearer of the wearable sensor device 152, in order to come to an approximation of data that represents overall patterns of the observations, while eliminating outlier (i.e., out-of-bound, anomalous) observations that are unwarranted/unsupported. Examples of such smoothing functions/algorithms/filters include, but are not limited to, additive smoothing algorithms, Kalman filters, least-squares fitting of polynomials (representing the subjective observations) algorithms, moving averages, exponential smoothing (to reduce random fluctuations in time series data), curve fitting of observational data, numerical smoothing and differentiation, etc.

For example, assume that an observer has made multiple past observations of the wearer of the wearable sensor device 152, and that the observations have varied not only due to the various states of the wearer (i.e., impairments of the wearer's cognitive state), but also to various states of the observer (i.e., the observer is hyper-alert, is sluggish, is angry, etc.), which affect whether or not the observer determines that there is an impairment to the cognitive state of the wearer of the wearable sensor device 152. Thus, in this embodiment, the observer of the wearer of the wearable sensor device sends multiple cognitive impairment state signals in response to the observer subjectively observing multiple instances of the impairment to the cognitive state of the wearer of the wearable sensor device, and the multiple cognitive impairment state signals are generated in response to the observer making multiple observations of the impairment to the cognitive state of the wearer of the wearable sensor device. In one embodiment, one or more processors apply a Kalman filter to the multiple observations of the impairment to the cognitive state of the wearer of the wearable sensor device. This Kalman filter uses a linear quadratic estimation to recursively remove anomalous observations from the multiple observations to generate a (in one embodiment, trusted) observation of the impairment to the cognitive state of the wearer of the wearable sensor device (i.e., wearable sensor device 152). An exemplary Kalman algorithm used for this determination is:

$$x_k = F_k x_{k-1} + B_k u_k + w_k$$

where $x_k$ is the (trusted) observation of the impairment to the cognitive state of the wearer of the wearable sensor device, $F_k$ is a predefined state transition model that is applied to a previous state $x_{k-1}$ of observed impairments to the cognitive state of the wearer of the wearable sensor device, $B_k$ is a predefined control-input model that is applied to a control vector $u_k$, and $w_k$ is erroneous observation noises that are drawn from a multivariate normal distribution $Q_k$, wherein $W_k$ is approximately equal to the set of numbers N from zero to $Q_k$ ($N(0, Q_k)$).

Continuing now with reference to FIG. 2, in response to observing a particular cognitive impairment state, the observer will initiate a "push" of data from the continuous circular buffer(s) 202 to the push data matrix 204, which is stored on a hardware storage device. As shown in FIG. 2, the cognitive impairment state 212 is represented by a digital value that is sent to the push data matrix 204. This digital value identifies a particular cognitive impairment state of the wearer of the wearable sensor device 152, which is defined by an observer of the wearer, such that precursive readings from the sensor(s) 208 are associated with a subsequent and specific cognitive impairment state and/or other related events (e.g., "benching" a sports player).

In one embodiment, the particular cognitive impairment state that is associated with specific precursive events (detected by the sensor(s) 208) is described by the wearer's own words and/or by the observer's own words. In another embodiment, the particular cognitive impairment state is selected from a menu or is otherwise predefined.

Continuing now with FIG. 2, assume that data from continuous circular buffer(s) 202 is continuously sent to accumulation data matrix 206. In this embodiment, accumulation data matrix 206 takes continuous readings from the continuous circular buffer(s) 202. However, each set of data that has been pushed to the push data matrix 204 is nonetheless identified within the accumulation data matrix 206. For example, data that was pushed to push data matrix 204 at the time of a "PUSH-A" is identified by block 214a; data that was pushed to push data matrix 204 at the time of a "PUSH-B" is identified by block 214b; and data that was pushed to push data matrix 204 at the time of a "PUSH-C" is identified by block 214c.

Data from blocks 214a-214c are then used to determine a Push Triggered Average (PTA), shown as push average matrix 216. Push average matrix 216 is calculated (e.g., by CIEAL 148 shown in FIG. 1) as one-third (assuming that three pushes occurred) of the sum of the values stored in each cell of the pushed buffers. That is, assume that a push results in three columns of nine cells. The values in the upper left cell in each of the blocks 214a-214c are summed together, divided by three, and the quotient (i.e., average) is then stored in the upper left cell of the push average matrix 216. Other cells in the 214a-214c are similarly summed together, divided by three, and their quotients (i.e., averages) are then stored in the corresponding cell of the push average matrix 216. This PTA (push average matrix 216) is then used as a "fuzzy" reference for new values pushed from the continuous circular buffer(s) 202. That is, PTA (push average value 216) provides a mean average for each of the sensed parameters. Ranges around these mean values (above and below) are predetermined, such that when values from the continuous circular buffer(s) 202 later fall within these ranges, a prediction can be made that the wearer will again experience (or is currently experiencing) the particular cognitive impairment state.

In one embodiment, a buffer data matrix 218 is generated from a single buffer in the push data matrix 204. For example, consider buffer b1 from push data matrix 204.

Assume that buffer b1 contains data from continuous circular buffer 210a that describe the heart rate of the user who is wearing the wearable sensor device 152. As depicted, b1 is broken down into three rows, r1-r3, in order to create the buffer data matrix 218. Buffer data matrix 218 is then used in a manner similar to that described herein for push data matrixes. That is, rather than require a push data matrix from multiple sensors, pushed (or alternatively, non-pushed but rather continuously streamed) data from a single sensor is converted into a matrix (buffer data matrix 218), which is then used to warn of an impending cognitive impairment state of the wearer by comparing this buffer data matrix 218 to known single-sensor data matrixes that are precursive to the particular cognitive impairment state of the user.

Note that while, as the name suggests, wearable sensor device 152/352/452/552 is presented as a wearable sensor device, in one or more embodiments the wearable sensor device 152/352/452/552 is a device that is simply proximate to, although not necessarily worn by, a user, such that ambient conditions, including biophysical traits of the user (e.g., frowns, smiles, flushed skin, etc.) are still sensed by sensors, such as sensors 208.

Figure 3:
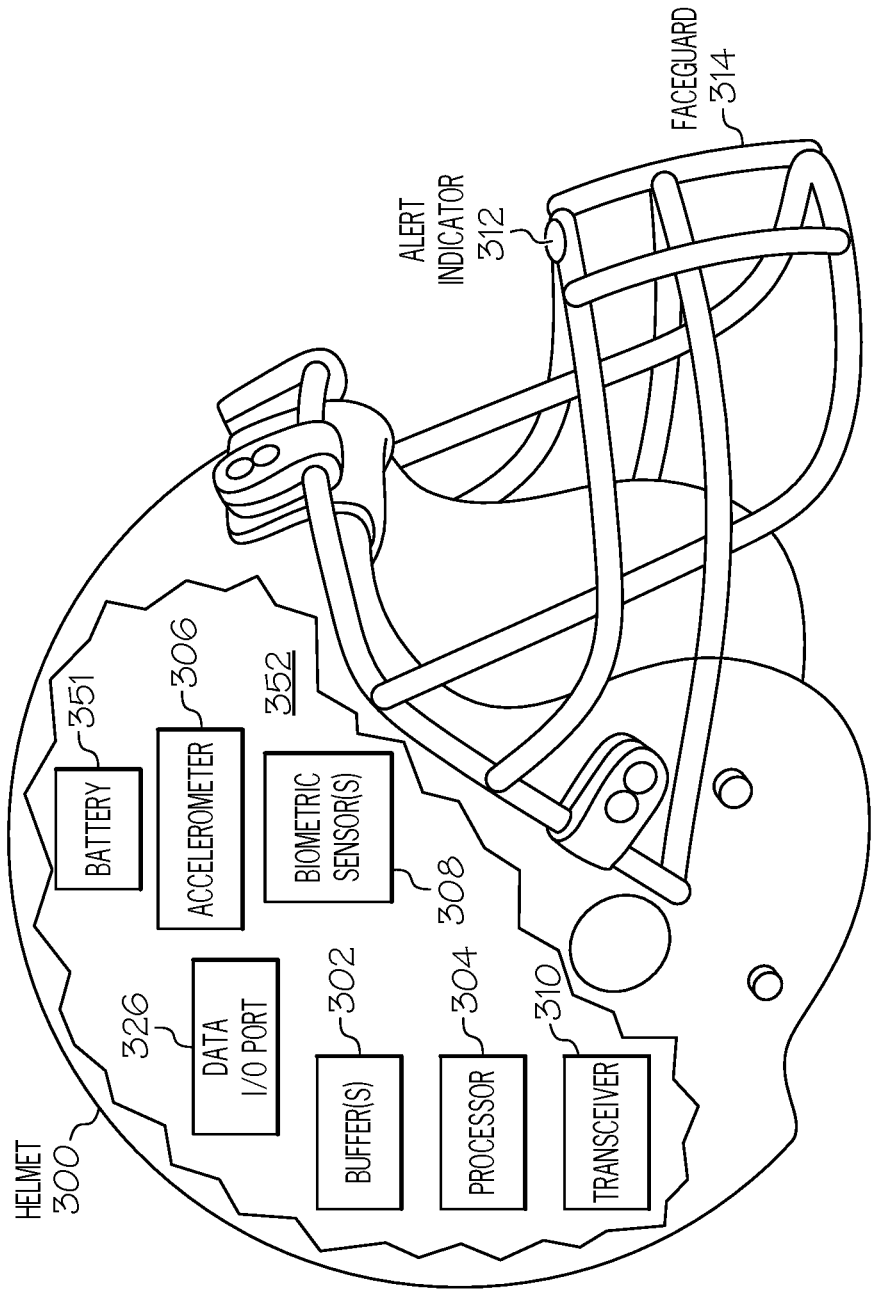
FIG. 3 depicts an exemplary wearable sensor device that is integrated into a sports helmet for monitoring physiological and physical conditions related to the sports helmet and its wearer.

In one embodiment, the wearable sensor device is integrated into a sport helmet. For example, as shown in FIG. 3, an exemplary wearable sensor device 352 is integrated into a sports helmet 300 for monitoring physiological and physical conditions related to the sports helmet and its wearer. One or more components of the exemplary wearable sensor device 352 are powered by a local battery 351 and/or an equivalent power source (e.g., a solar cell).

In one embodiment, the wearable sensor device 352 includes one or more biometric sensor(s) 308, which measure physiological states (i.e., perspiration, skin temperature, eye flutter, voice articulations such as grunts of pain, etc.) of the wearer, similar to the sensors 208 described above. In addition, the wearable sensor device 352 includes an accelerometer 306. The accelerometer 306, which may be any known electro-mechanical device that measures acceleration, including rapid deceleration, detects whether the helmet 300 has been subjected to a sharp blow (as indicated by a sudden acceleration/deceleration detected by the accelerometer 306), initiated by the wearer or by another player. Note that any blow that occurs when the player is not actually wearing the helmet 300 (e.g., while being transported to the game, if jostled within a gym bag, etc.) is irrelevant to the cognitive state of the athlete. Thus, in one embodiment the battery 351 is only connected when the athlete puts on the helmet 300. This selective powering on/off may be from a sensor switch (not shown, but within the interior lining of the helmet 300), a manual switch (also not shown), etc.

A processor 304 processes readings from the biometric sensor(s) 308 and/or the accelerometer 306 by loading them into buffer(s) 302, which in one embodiment have the same architecture and function as the continuous circular buffer(s) 202 shown in FIG. 2.

A data I/O port 326 (which in one embodiment has a same architecture as USB port(s) 126 shown in FIG. 1) is able to 1) download data from the buffer(s) 302, and 2) upload markers into the buffer(s) 302.

Thus, in the embodiment of the present invention in which a wearable sensor device 352 is integrated into a sports helmet 302, the wearable sensor device 352 includes a physiological sensor such as one or more of the biometric sensor(s) 308. These biometric/physiological sensors detect a biological state of the wearer of the sports helmet 302, such as his/her heart rate, perspiration level, skin temperature, EEG and/or EKG, oxygen saturation level, etc. In this embodiment, the wearable sensor device 352 also includes an accelerometer sensor, such as accelerometer 306. This accelerometer sensor detects a change in velocity (e.g., a crash into another player's helmet, striking the ground or other immovable object, etc.).

Also part of the wearable sensor device 352 is a first buffer (i.e., one of the buffer(s) 302 shown in FIG. 3). This first buffer (which in one embodiment is implemented as a dedicated hardware storage device—"hardware buffer") is communicatively coupled to the physiological sensor (biometric sensor(s) 308) and the accelerometer sensor (accelerometer 306), and thus is able to store a first set of time-dependent sensor readings (i.e., sensor readings from the biometric sensor(s) 308 and/or the accelerometer 306 which are retrieved/recorded in linear time (sequentially)).

The wearable sensor device 352 also includes a receiver (e.g., part of transceiver 310) for receiving a first cognitive impairment state signal. That is, when an observer of a wearer of the wearable sensor device (wearable sensor device 352 integrated into helmet 302) subjectively observes an impairment to a cognitive state of the wearer of the wearable sensor device/helmet, the observer sends the first cognitive impairment state signal to the transceiver 310. A data insertion logic (e.g., part of processor 304) then inserts a cognitive impairment state marker at a predefined position in the first buffer.

Thereafter, a second buffer (i.e., one of the buffer(s) 302, and which may be the same as the first buffer if steps are taken to clear and save data from the first buffer for further use), initiates loading of a second set of time-dependent sensor readings from the physiological sensor and the accelerometer sensor. For example assume that the wearer of the helmet 302 is a contact sport (e.g., American football) player. The first buffer may store data from the biometric sensor(s) 308 and/or the accelerometer 306 taken during a first game. Thereafter, the second buffer may store data from biometric sensor(s) 308 and/or the accelerometer 306 taken during a later game (e.g., played the following week).

That is, assume that the first buffer contains the following sensor readings from the biometric sensor(s) 308 (identified as "Bx") and the accelerometer 306 (identified as "Ax"): B1, B2, B3, A1, A2, A3. As described herein, "Bx" and "Ax" are time-dependent, meaning that they are stored in the first buffer as they are generated by their respective sensors. For purposes of illustration, assume then that the cognitive impairment state marker (identified as "I") is placed after "Bx" and "Ax", thus giving the temporal sequence of: B1, B2, B3, A1, A2, A3, I.

A hardware comparator (e.g., part of processor 304) then compares time-dependent sensor readings from the first buffer up to the predefined position with time-dependent sensor readings from the second buffer. For example, assume again that the first buffer contains the sensor readings B1, B2, B3, A1, A2, A3, which are stored before the cognitive impairment state marker I. Assume also that the second buffer contains the sensor readings B1, B2, A1, A2. Although B1, B2, A1, A2 is not the same as B1, B2, B3, A1, A2, A3, the present invention recognizes that the wearer is taking actions that have a similar pattern as those recorded during the last game. Thus, the present invention provides an "intervention" with the wearer of the helmet, giving the wearer the opportunity to perform evasive actions (i.e., stop tackling with his helmet, being less aggressive, etc.) to avoid reaching the pattern B1, B2, B3, A1, A2, A3, which prompted the earlier signal (and thus cognitive impairment state marker I) from the observer.

Note that in one embodiment of the present invention, the cognitive impairment state marker I is also part of the precursive pattern that warns of an impending impaired cognitive state. In this embodiment, the cognitive impairment state marker I functions as a warning during future activities. For example, the cognitive impairment state marker I, along with the sensor readings B1, B2, B3, A1, A2, A3, would produce a pattern of B1, B2, B3, A1, A2, A3, I. Assume that the pattern B1, B2, B3, A1, A2, A3 is recorded a subsequent event (meeting, sports game, etc.) for the wearer of the wearable sensor device. This newly-derived pattern B1, B2, B3, A1, A2, A3 will then cause the system to recognize "I" as the next data point, which causes a warning to be issued to the wearer of the wearable sensor device. That is, at this point, the wearer of the wearable sensor device may not be presenting evidence of an impaired cognitive state, either internally (i.e., the wearer of the wearable sensor device does not yet "feel" the impaired cognitive state) or to another (i.e., the observer of the wearable sensor device does not perceive that the wearer of the wearable sensor device has entered into the impaired cognitive state). However, a warning, triggered by the "I" after the newly-recorded pattern of B1, B2, B3, A1, A2, A3, will give the wearer additional warning that an impaired cognitive state is impending. In one or more embodiments, this intervention signal (indicated by the cognitive impairment state marker I) and/or the warning derived therefrom is used as part of the $B_k$ predefined control-input model that is applied to a control vector $u_k$ in the Kalman filter described herein.

Thus, an alert generator (e.g., part of processor 304), in response to a partial match of the first set of time-dependent sensors readings up to the predefined position and the second set of time-dependent sensors readings sensor readings reaching a predefined match level, issues an alert to the wearer of the wearable sensor device. That is, in the example presented above, if the second buffer stores the pattern B1, B2, A1, A2, then a predefined match level (e.g., 4 out of 6 of the sensor readings B1, B2, B3, A1, A2, A3) has been reached. This triggers the alert generator to send a signal to the wearer of the helmet, such as sending a color-coded signal to a multi-color light emitting diode (LED) device 312 mounted on the faceguard 314 of the helmet 302.

If capable of selectively displaying different colors, the LED device 312 may turn yellow if the alert is to let the wearer know that continuing the same style of play will result in receiving a second cognitive impairment state signal from the observer. For example, this second cognitive impairment state signal may result in the player being prevented from further play, being required to take additional instruction, being required to submit to a medical examination, etc.

Similarly, the LED device 312 may turn red if the alert advises the wearer of the wearable sensor device to take an evasive action that has been predetermined to avoid experiencing an impairment to the cognitive state of the wearer. That is, if the player continues to play in the same manner, the red alert signal indicates to the wearer that continuing this style of play will result in the same impairment (e.g., disorientation, confusion, etc.) that was observed before. In one embodiment, the red alert signal may result in the player being immediately taken out of the game.

While the present invention has been described above in the context of a sporting event, in another embodiment the present invention is applied to a non-sporting event. For example, in another embodiment, the wearable sensor device is simply worn on the wrist. Thus, and with reference now to FIG. 4, consider the wearable sensor device 452, which is structurally similar to the wearable device 152 shown in FIG. 2, and includes sensors such as sensor(s) 208, a power supply (not shown), buffers (e.g., continuous circular buffer(s) 202), etc. needed for a wearable sensor device as presented herein. As shown, wearable sensor device 452 (which may be worn on the wrist) includes a keypad 402. In one embodiment, keys on the keypad are pre-programmed for a particular cognitive state. For example, one of the keys may be for "boredom". Thus, if the user is experiencing "boredom", then the user pushing the button for "boredom" causes data from the continuous circular buffer(s) 202, along with a flag/signal that is associated with the cognitive impairment state 212 for "boredom" (and identified by pushing the key on keypad 402 for "boredom"), to be sent to the push data matrix 204 in FIG. 2. Similarly, if the user is experiencing "anxiety", then data from the continuous circular buffer(s) 202, along with a flag/signal that is associated with the cognitive impairment state 212 for "anxiety" (and identified by pushing the key on keypad 402 for "anxiety"), is sent to the push data matrix 204 in FIG. 2 when the user pushes the "anxiety" button on the keypad 402. Thus, if an observer of the wearer of the wearable sensor device 452 depicted in FIG. 4 decides that the wearer is exhibiting boredom or anxiety, this observation can be confirmed by the wearer's own personal sensation.

Figure 4:
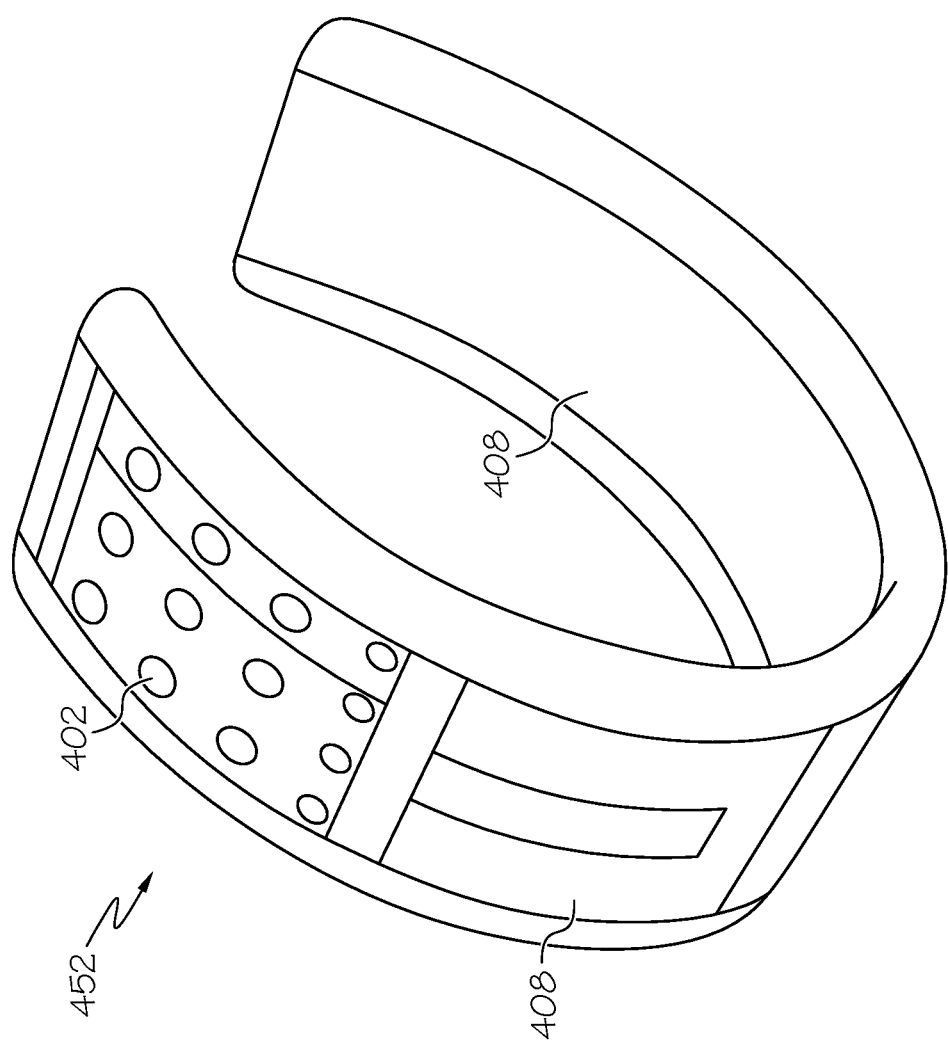
FIG. 4 illustrates an exemplary wrist-wearable sensor device for sensing user physiological and/or other conditions of a wearer of the device.

Note that in one embodiment, the wearable sensor device 452 shown in FIG. 4 includes both biophysical (unique to the user) and ambient environmental sensors. More specifically, wearable sensor device 452 includes biometric sensors that, depending on their structure, configuration, and/or positioning on the wearable sensor device 452, are able to monitor biometric conditions (e.g., blood pressure, heart rate, etc.), musculoskeletal motions (e.g., cameras that track a user's facial expressions, motion sensors that track a user's walking gait, etc.) and other biophysical features/conditions of the user, but also can track ambient environmental conditions (e.g., local sounds, light, moisture, air temperature, etc.).

Figure 5:
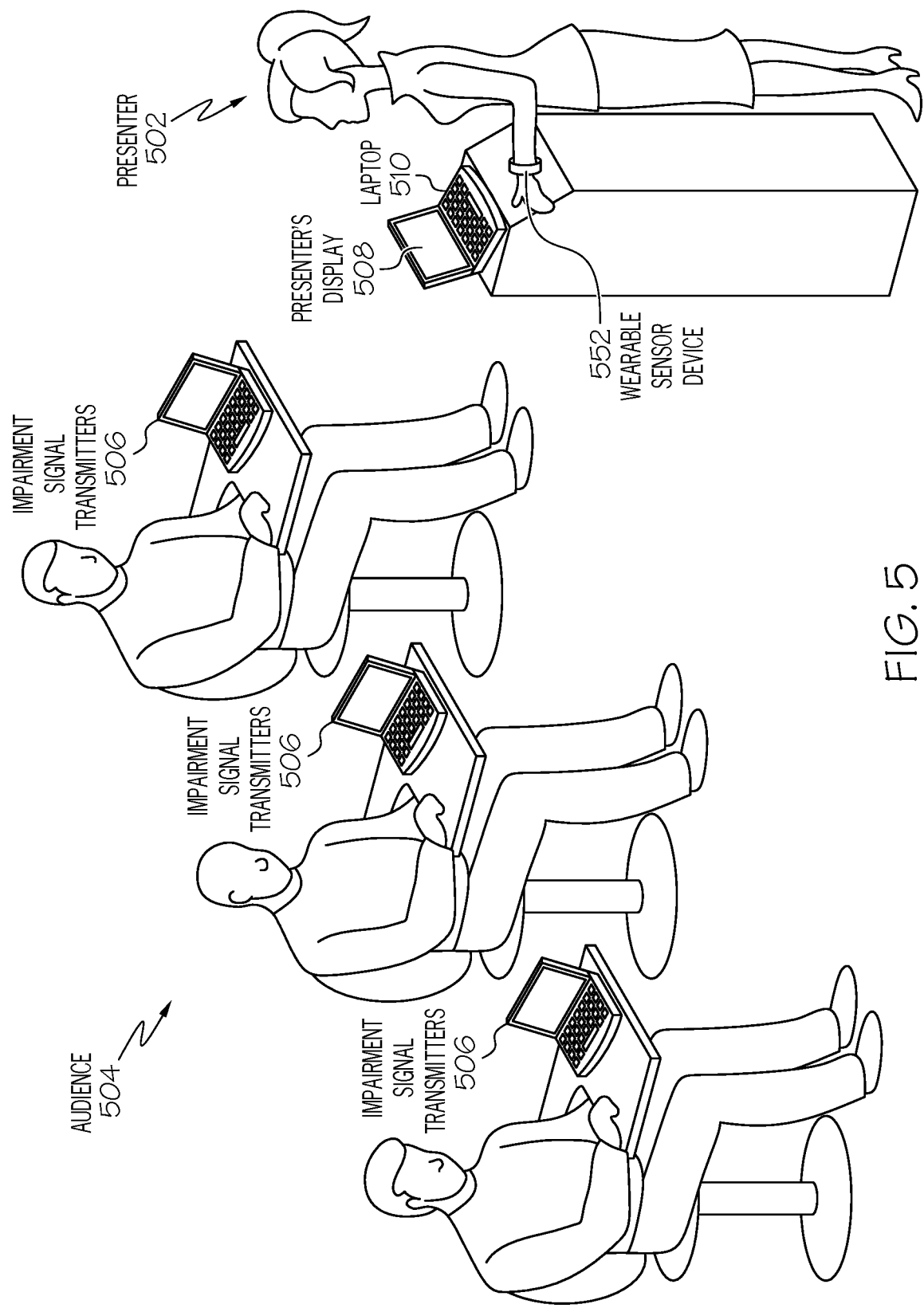
FIG. 5 depicts a wearer of the wrist-wearable sensor device illustrated in FIG. 4 while speaking before an interactive audience.

With reference now to FIG. 5, consider the scenario in which a wearer of the wrist-wearable sensor device is a person making a presentation (i.e., presenter 502) to an audience 504. Note that the presenter 502 is wearing a wearable sensor device 552, which has the same hardware and configuration as the wearable sensor device 452 depicted in FIG. 4. During the presentation given by presenter 502, members of the audience are able to input cognition state impairment signals via impairment signal transmitters 506. For example, if one or more of the members of the audience 504 perceive that the presenter 502 is boring or anxious or otherwise doing poorly, then this information may be displayed on the presenter's display 508 on his/her laptop 510. If only a few members of the audience feel that the presenter 502 is doing poorly, then the presenter 502 may still have time to salvage the presentation. However, and in accordance with a preferred embodiment of the present invention, if a threshold of the members of the audience 503 (e.g., 50%) indicate that the presenter 502 is doing poorly, then it is too late to salvage the current presentation. However, the presenter 502 still has useful data points for future presentations. That is, if the wearable sensor device 552 detects a similar pattern progression as that which ultimately led to the previous audience's negative response, then a signal on the presenter's display 508 will offer suggestions to avoid (execute avoidance actions) another poor performance. In one or more embodiments of the present invention, these suggestions are defined as part of the $B_k$ predefined control-input model that is applied to a control vector $u_k$ of the Kalman filter described herein.

For example, at the subsequent presentation, if the presenter 502 is once again moving about too much (as detected by sensors in the wearable sensor device 552), the presenter's display 508 may present a suggestion to "Stand Still". That is, in the previous presentation, excessive movement by the presenter 502 (i.e., pacing back and forth, excessive hand/body gestures, etc.) led the previous audience to subjectively determine that the presenter 502 was "frenetic". If the presenter 502 again displays such excessive movement during a subsequent/current presentation, then the system will advise him/her to modulate his body movements (e.g., with the suggestion that he/she "Stand Still").

Figure 6:
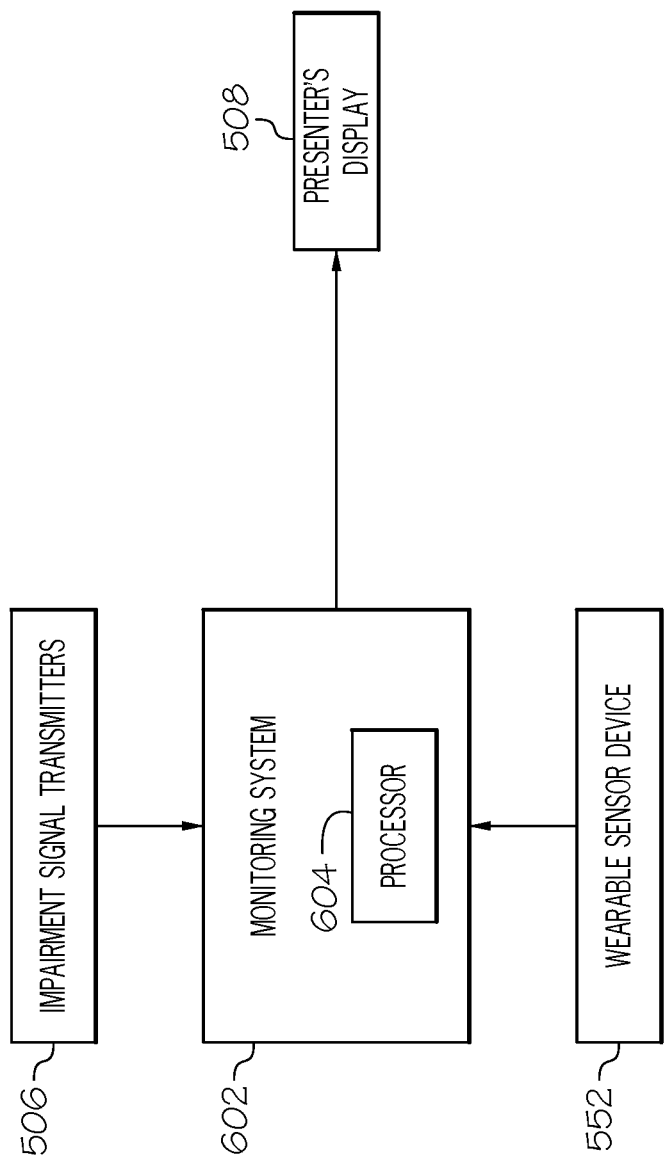
FIG. 6 illustrates a high-level block diagram of an exemplary networked system used in the embodiment depicted in FIG. 5.

FIG. 6 illustrates a high-level block diagram of an exemplary networked system used in the embodiment depicted in FIG. 5. That is, a monitoring system 602 (e.g., computer 102 shown in FIG. 1) receives inputs from the audience (via their impairment signal transmitters 506) and the presenter (via his/her wearable sensor device 552). The monitoring system 602, using a processor 604 (analogous to the processor 104 shown in FIG. 1) compares sensor patterns from previous presentations given by the presenter 502 with current sensor patterns. If the monitoring system 602 detects that a similar pattern is being followed (although not up to the point of losing the audience's attention/approval), then an alert and/or suggestion is sent to the presenter's display 508.

Figure 7:
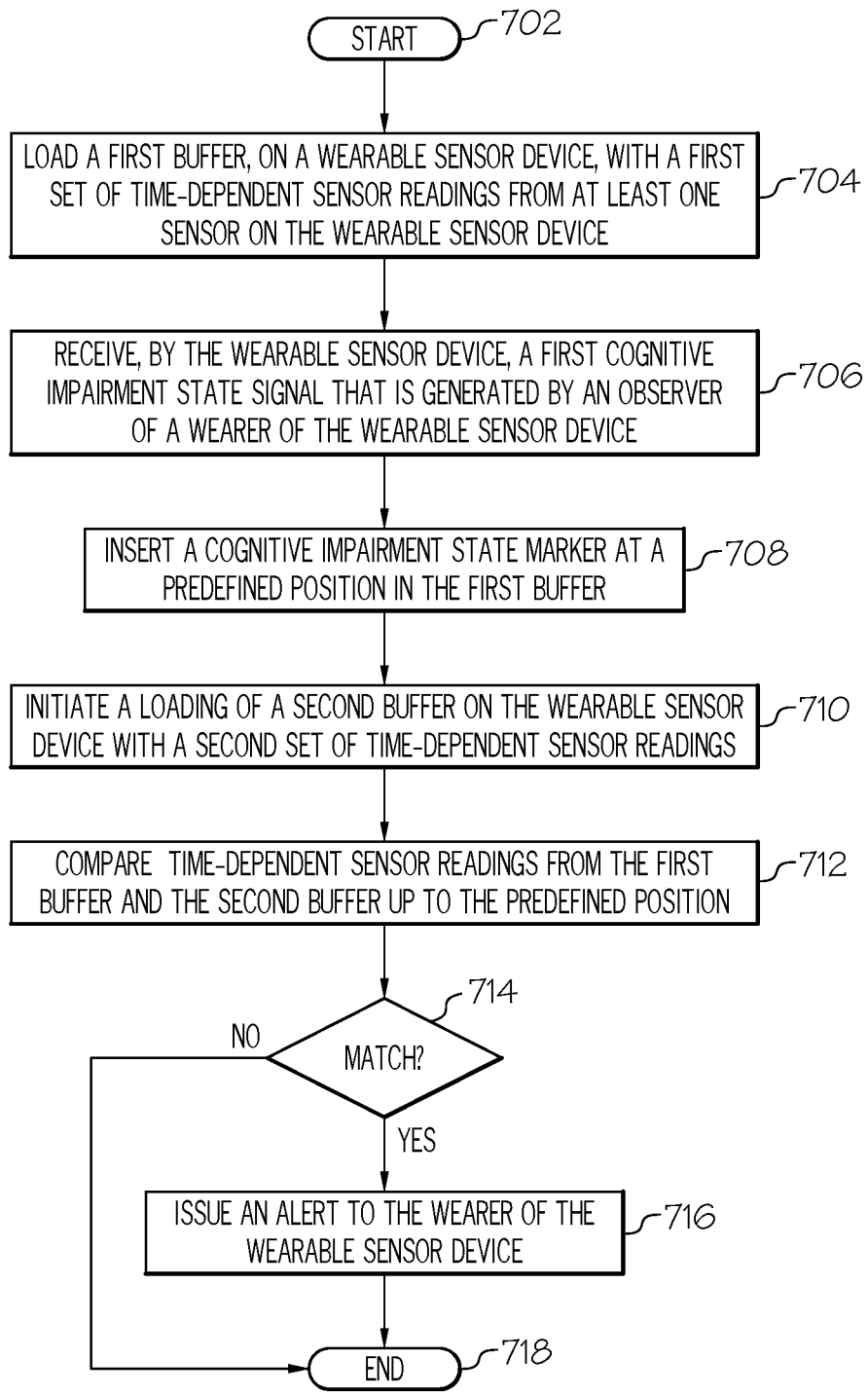
FIG. 7 is a high-level flowchart of one or more steps performed by one or more processors to guide evasive actions for avoiding effects of an impaired cognitive state.

With reference now to FIG. 7, a high-level flowchart of one or more steps performed by one or more processors to guide evasive actions for avoiding effects of an impaired cognitive state is presented. Again, note that one or more of the steps depicted may be performed by one or more processors (e.g., processor 104 in FIG. 1, processor 304 in FIG. 3, processor 604 in FIG. 6, etc.)

After initiator block 702, a first buffer is loaded on a wearable sensor device with a first set of time-dependent sensor readings (block 704). As described herein, the first buffer is communicatively coupled to at least one sensor on the wearable sensor device.

As described in block 706, the wearable sensor device receives a first cognitive impairment state signal. As described herein, this first cognitive impairment state signal is generated by an observer of a wearer of the wearable sensor device in response to the observer subjectively observing an impairment to a cognitive state of the wearer of the wearable sensor device. For example, if the observer thinks that the wearer of the wearable sensor device appears to be confused, boring, anxious, etc., then the observer will generate the first cognitive impairment state signal. In one embodiment, this first cognitive impairment state signal is transmitted from a transmitter (e.g., one or more of the impairment signal transmitters 506 shown in FIG. 5). In one embodiment, this first cognitive impairment state signal is an automatic consequence of taking the step of downloading data from the sensor data buffer (e.g., buffer(s) 302 in FIG. 3) via a data I/O port (e.g., data I/O port 326 in FIG. 3).

As described in block 708, a cognitive impairment state marker is then inserted at a predefined position in the first buffer. This cognitive impairment state marker (e.g., "I" presented above) is inserted at the predefined position in the first buffer in response to the wearable sensor device receiving the first cognitive impairment state signal.

As described in block 710, loading of a second buffer on the wearable sensor device with a second set of time-dependent sensor readings from at least one sensor on the wearable sensor device is initiated. Thus, as described above, sensor reading B1 may be loaded, followed by sensor readings B1, A1, followed by sensor readings B1, A1, A2, etc.

As described in block 712, time-dependent sensor readings from the first buffer up to the predefined position are then compared with time-dependent sensor readings from the second buffer. In response to a partial match of the first set of time-dependent sensors readings up to the predefined position and the second set of time-dependent sensors readings (now being taken in real time) reaching a predefined match level (query block 714), then an alert is issued to the wearer of the wearable sensor device (block 716).

The predefined match level may be numeric, weighted, etc. For example, assume that the first buffer contains the sensor readings B1, A1, A2, B2, B3, B4 (where "B" indicates a biometric sensor reading and "A" indicates an accelerometer reading). After storing B1, A1, A2, B2, B3, B4 in the first buffer, the system receives a cognitive impairment state marker "I", which indicates that there is an observed impairment to the cognitive state of the wearer of the wearable sensor device, and thus "I" is placed after the sensor readings B1, A1, A2, B2, B3, B4 in the first buffer.

Assume now that the second buffer (or the first buffer after being cleared and its contents stored in a local memory for use in comparison to new sensor data) contains the sensor readings B1, A1, A2, B2. The "predefined match level" needed to initiate the alert may simply be a percentage, such as 50%. Thus, 50% of the six sensor readings B1, A1, A2, B2, B3, B4 would be three, regardless of which sensor readings are subsequently taken and stored in the second buffer.

However, in another embodiment, each of the sensor readings B1, A1, A2, B2, B3, B4 may be weighted. For example, sensor readings from the accelerometer (A1, A2, A3, etc.) may be predetermined to be more important, and thus weighted more heavily, than sensor readings form the biometric sensors (B1, B2, B3, etc.). Thus, as few as one or two accelerometer events (A1, A2) may be enough to trigger the alert, even without any biometric events (B1, B2, etc.).

The flow-chart of FIG. 7 ends at terminator block 718.

As described herein, in one embodiment of the present invention the alert to the wearer of the wearable sensor device advises the wearer of the wearable sensor device to take an evasive action that has been predetermined to avoid receiving a second cognitive impairment state signal from the observer. That is, the alert may advise the wearer to take corrective/ameliorative steps to avoid being told again that his/her style of play is dangerous, he/she is boring, etc.

As described herein, in one embodiment of the present invention the alert to the wearer of the wearable sensor device advises the wearer of the wearable sensor device to take an evasive action that has been predetermined to avoid experiencing an impairment to the cognitive state of the wearer. That is, the alert may advise the wearer of the wearable sensor device that his/her style of play will actually cause him/her to be disoriented, that his/her presentation style will be boring, etc., even if nobody tells him/her.

In one embodiment of the present invention, the first set of time-dependent sensor readings are analyzed, in order to identify a cause of the impairment to the cognitive state of the wearer. For example, assume that historical records show that when events that result in sensor readings A1, A1, A3, B1, B2, B3 ultimately lead to a state of dementia, a conclusion is reached that these events are the cause of the state of dementia. Assuming that such records and conclusions are available, then in one embodiment they are used to verify the observations of the observer of the wearer of the wearable sensor device.

As described herein, in one embodiment of the present invention the first buffer and the second buffer in the wearable sensor device are both continuous circular buffers, in which each stores data from a different sensor in the wearable sensor device. In this embodiment, a cause of the impairment to the cognitive state of the wearer of the wearable sensor device is predicted by a probability formula:

$$P(M|E) = \frac{P(E|M)}{\sum_m P(E|Mm)P(Mm)} * P(M)$$

where:
P(M|E) is a probability that the impairment to the cognitive state will occur (M) given that (|) data from the continuous circular buffers falls within a predefined Push Triggered Average (PTA—described above) of previously pushed data from the continuous circular buffers (E);
P(E|M) is a probability that data from the continuous circular buffers falls within the predefined PTA of previously pushed data from the continuous circular buffers (E) given that (|) the impairment to the cognitive state of the wearer is actually occurring (M);
P(M) is a probability that the impairment to the cognitive state of the wearer will occur regardless of any other information; and
Σm is a sum of all occurrences m, for the probability P(E|M) times the probability P(M).

In one embodiment of the present invention, predicting whether the impairment to the cognitive state of the wearer of the wearable sensor device will occur is based on a statistical analysis of the subsequent set of sensor readings compared to the pushed sensor readings, wherein a match within a predefined statistical range between the subsequent set of sensor readings and the pushed sensor readings leads to the prediction of the impairment to the cognitive state of the wearer of the wearable sensor device. That is, if the previous sensor readings align with current sensor readings within a statistically significant range, then an assumption/prediction is made that a recurrence of the cognitive impairment state is likely.

As described herein, in one embodiment of the present invention the predefined position in the first buffer at which the cognitive impairment state marker is inserted is at an end of the first set of time-dependent sensor readings. In this embodiment, a determination is made that sensor readings stored prior to the end of the first set of time-dependent sensor readings are precursors to the impairment to the cognitive state of the wearer of the wearable sensor device. That is if the sensor readings B1, B2, B3, A1, A2, A3 lead to the insertion of the cognitive impairment state marker I at their end, then a conclusion is reached that the events that caused sensor readings B1, B2, B3, A1, A2, A3 lead to the cognitive impairment state reflected by "I".

In one embodiment of the present invention, the first set of time-dependent sensor readings are made up of a first subset of time-dependent sensor readings and a second subset of time-dependent sensor readings. The first subset of time-dependent sensor readings record event states that occur before event states that are represented by the second subset of time-dependent sensor readings. For example, a set of sensor readings B1, A1, A2, B2, B3, A3 may be made up of a first subset of sensor readings B1, A1, A2, which occur before a second subset of sensor readings B2, B3, A3 (i.e., the events that caused sensor readings B1, A1, A2 occurred before events that caused sensor readings B2, B3, A3). Similarly, the second set of time-dependent sensor readings comprise a third subset of time-dependent sensor readings and a fourth subset of time-dependent sensor readings, where the third subset of time-dependent sensor readings record event states that occur before event states that are represented by the fourth subset of time-dependent sensor readings. For example, the third subset found at the beginning of the second set of time-dependent sensors may be B1, A1, A2. Since the first subset and the third subset are identical (B1, A1, A2), then a conclusion is reached that the wearer of the wearable sensor device is headed for a specific cognitive impairment state, regardless of the contents of the fourth subset of time-dependent sensor readings in the second set of time-dependent sensor readings, and an alert is issued.

As noted herein, in one or more embodiments of the present invention the sensors in the wearable sensor device detect physiological states of the user, musculoskeletal bodily acts of the user, keywords spoken by the user, a quality of a voice pattern from the user, and ambient environmental conditions around the user. Thus, specific patterns of sensor readings from all of these sensors are used to provide a warning of a recurrence of a particular impairment to the cognitive state of the wearer of the wearable sensor device.

Note that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:
1. A method comprising:
    detecting, by a physiological sensor in a helmet, a biological state of a wearer of the helmet;
    detecting, by an accelerometer sensor in the helmet, a change in velocity of the helmet;
    storing, into a first buffer in the helmet, a first set of time-dependent sensor readings from the physiological sensor and the accelerometer sensor in the helmet;
    receiving, by a receiver in the helmet, a first cognitive impairment state signal, wherein the first cognitive impairment state signal is sent by a human observer of the wearer of the helmet in response to the human observer subjectively observing an impairment to a cognitive state of the wearer of the helmet, and wherein the human observer and the wearer of the helmet are different persons;
    inserting, by one or more processors in the helmet, a cognitive impairment state marker in the first buffer in the helmet, wherein the cognitive impairment state marker is set at a position that is associated with the receiver in the helmet receiving the first cognitive impairment state signal;

loading, by the one or more processors in the helmet, a second set of time-dependent sensor readings from the physiological sensor and the accelerometer sensor into a second buffer in the helmet, wherein the second set of time-dependent sensor readings is generated after the receiver in the helmet receives the first cognitive impairment state signal;

comparing, by one or more processors in the helmet, the first set of time-dependent sensor readings up to the cognitive impairment state marker to the second set of time-dependent sensor readings;

determining, by one or more processors in the helmet, that the first set of time-dependent sensor readings up to the cognitive impairment state marker matches the second set of time-dependent sensor readings; and in response to determining that the first set of time-dependent sensor readings up to the cognitive impairment state marker matches the second set of time-dependent sensor readings, activating, by one or more processors in the helmet, an alert indicator in the helmet, wherein the alert indicator is a physical device that warns the wearer of the helmet of an impending recurrence of an impaired cognitive state for the wearer of the helmet.

2. The method of claim 1, wherein the alert indicator advises the wearer of the helmet to take an action that has been predetermined to avoid receiving a second cognitive impairment state signal from the observer.

3. The method of claim 1, wherein the alert indicator advises the wearer of the helmet to take an action that has been predetermined to avoid experiencing an impairment to the cognitive state of the wearer.

4. The method of claim 1, wherein the helmet is worn by the wearer during a first game and a second game that occurs after the first game, wherein the first set of time-dependent sensor readings is generated during the first game and the second set of time-dependent sensor readings is generated during the second game.

5. The method of claim 4, wherein the first buffer is dedicated to storing the first set of time-dependent sensor readings from the first game and the second buffer is dedicated to storing the second set of time-dependent sensor readings from the second game.

6. The method of claim 1, wherein the alert indicator is a multi-color light emitting diode (LED) device, and wherein the method further comprises:

determining, by the one or more processors in the helmet, a first pattern of sensor readings in the first set of time-dependent sensor readings up to the cognitive impairment state marker and a second pattern of sensor readings in the second set of time-dependent sensor readings;

determining, by the one or more processors in the helmet, a match level between the first pattern and the second pattern; and in response to determining that the match level reaches a predefined match level, generating, by the one or more processors, a color-coded signal from the multi-color LED device that indicates a likelihood of the wearer of the helmet experiencing a recurrence of the impairment to the cognitive state of the wearer of the helmet.

7. The method of claim 1, wherein the first buffer and the second buffer are both continuous circular buffers, and wherein a cause of the impairment to the cognitive state of the wearer of the wearable sensor device is predicted by a probability formula:

$$P(M \mid E) = \frac{P(E \mid M)}{\sum m P(E \mid Mm) P(Mm)} * P(M)$$

where:
P(M|E) is a probability that the impairment to the cognitive state will occur (M) given that (I) data from the continuous circular buffers (E) falls within a predefined Push Triggered Average (PTA) of previously pushed data from the continuous circular buffers (E);

P(E|M) is a probability that data from the continuous circular buffers falls within the predefined PTA of previously pushed data from the continuous circular buffers (E) given that (I) the impairment to the cognitive state of the wearer is actually occurring (M);

P(M) is a probability that the impairment to the cognitive state of the wearer will occur regardless of any other information; and Σm is a sum of all occurrences m, for the probability P(E|M) times the probability P(M).

8. The method of claim 1, further comprising:
determining, by sensors in the helmet, that the wearer is not currently wearing the helmet; and
blocking, by one or more processors, any accelerometer sensor readings from being stored in the first buffer while the wearer is not currently wearing the helmet.

9. The method of claim 1, wherein multiple cognitive impairment state signals are sent by the human observer to the receiver in the helmet based on observations of the human observer, and wherein untrusted anomalous cognitive impairment state signals are blocked from being sent from the human observer to the receiver in the helmet by identifying trusted observations of the human observer based on:

$$x_k = F_k x_{k-1} + B_k u_k + w_k;$$

wherein $x_k$ is a trusted observation of the impairment to the cognitive state of the wearer of the wearable sensor device, $F_k$ is a predefined state transition model that is applied to a previous state $x_{k-1}$ of observed impairments to the cognitive state of the wearer of the wearable sensor device, $B_k$ is a predefined control-input model that is applied to a control vector $u_k$ and $w_k$ is erroneous observation noises that are drawn from a multivariate normal distribution $O_k$, wherein $w_k$ is equal to a set of numbers N from zero to $O_k$ (N(0, $O_k$)).

10. The method of claim 1, further comprising:
receiving, by one or more processors, spoken words of the wearer of the helmet after the change in the velocity of the helmet;
extracting, by one or more processors, semantic vectors from the spoken words as features in order to compute a vector distance between the spoken words and specific neurological states; and
further identifying, by one or more processors, the impairment of the wearer of the helmet based on the vector distance between the spoken words and the specific neurological states.

11. A computer program product for controlling an alert indicator in a helmet, the computer program product comprising a non-transitory computer readable storage medium having program instructions embodied therewith, the program instructions readable and executable by a computer to perform a method comprising:

detecting, by a physiological sensor in the helmet, a biological state of a wearer of the helmet;

detecting, by an accelerometer sensor in the helmet, a change in velocity of the helmet;

storing, into a first buffer in the helmet, a first set of time-dependent sensor readings from the physiological sensor and the accelerometer sensor in the helmet;

receiving, by a receiver in the helmet, a first cognitive impairment state signal, wherein the first cognitive impairment state signal is sent by a human observer of the wearer of the helmet in response to the human observer subjectively observing an impairment to a cognitive state of the wearer of the helmet, and wherein the human observer and the wearer of the helmet are different persons;

inserting a cognitive impairment state marker in the first buffer in the helmet, wherein the cognitive impairment state marker is set at a position that is associated with the receiver in the helmet receiving the first cognitive impairment state signal;

loading a second set of time-dependent sensor readings from the physiological sensor and the accelerometer sensor into a second buffer in the helmet, wherein the second set of time-dependent sensor readings is generated after the receiver in the helmet receives the first cognitive impairment state signal;

comparing the first set of time-dependent sensor readings up to the cognitive impairment state marker to the second set of time-dependent sensor readings;

determining that the first set of time-dependent sensor readings up to the cognitive impairment state marker matches the second set of time-dependent sensor readings; and in response to determining that the first set of time-dependent sensor readings up to the cognitive impairment state marker matches the second set of time-dependent sensor readings, activating an alert indicator in the helmet, wherein the alert indicator is a physical device that warns the wearer of the helmet of an impending recurrence of an impaired cognitive state for the wearer of the helmet.

12. The computer program product of claim 11, wherein the alert indicator advises the wearer of the helmet to take an action that has been predetermined to avoid receiving a second cognitive impairment state signal from the observer.

13. The computer program product of claim 11, wherein the alert indicator advises the wearer of the helmet to take an action that has been predetermined to avoid experiencing an impairment to the cognitive state of the wearer.

14. The computer program product of claim 11, wherein the helmet is worn by the wearer during a first game and a second game that occurs after the first game, wherein the first set of time-dependent sensor readings is generated during the first game and the second set of time-dependent sensor readings is generated during the second game.

15. The computer program product of claim 14, wherein the first buffer is dedicated to storing the first set of time-dependent sensor readings from the first game and the second buffer is dedicated to storing the second set of time-dependent sensor readings from the second game.

16. The computer program product of claim 11, wherein the alert indicator is a multi-color light emitting diode (LED) device, and wherein the method further comprises:

determining a first pattern of sensor readings in the first set of time-dependent sensor readings up to the cognitive impairment state marker and a second pattern of sensor readings in the second set of time-dependent sensor readings;

determining a match level between the first pattern and the second pattern; and in response to determining that the match level reaches a predefined match level, generating a color-coded signal by the multi-color LED device that indicates a likelihood of the wearer of the helmet experiencing a recurrence of the impairment to the cognitive state of the wearer of the helmet.

17. The computer program product of claim 11, wherein the program instructions are provided as a service in a cloud environment.

18. A computer system comprising one or more processors, one or more computer readable memories, and one or more computer non-transitory computer readable storage media, and program instructions stored on at least one of the one or more non-transitory storage media for execution by at least one of the one or more processors via at least one of the one or more memories, the stored program instructions comprising:

program instructions to detect, by a physiological sensor in a helmet, a biological state of a wearer of the helmet;

program instructions to detect, by an accelerometer sensor in the helmet, a change in velocity of the helmet;

program instructions to store, into a first buffer in the helmet, a first set of time-dependent sensor readings from the physiological sensor and the accelerometer sensor in the helmet;

program instructions to receive, by a receiver in the helmet, a first cognitive impairment state signal, wherein the first cognitive impairment state signal is sent by a human observer of the wearer of the helmet in response to the human observer subjectively observing an impairment to a cognitive state of the wearer of the helmet, and wherein the human observer and the wearer of the helmet are different persons;

program instructions to insert a cognitive impairment state marker in the first buffer in the helmet, wherein the cognitive impairment state marker is set at a position that is associated with the receiver in the helmet receiving the first cognitive impairment state signal;

program instructions to load a second set of time-dependent sensor readings from the physiological sensor and the accelerometer sensor into a second buffer in the helmet, wherein the second set of time-dependent sensor readings are generated after the receiver in the helmet receives the first cognitive impairment state signal;

program instructions to compare the first set of time-dependent sensor readings up to the cognitive impairment state marker to the second set of time-dependent sensor readings;

program instructions to determine that the first set of time-dependent sensor readings up to the cognitive impairment state marker matches the second set of time-dependent sensor readings; and program instructions to, in response to determining that the first set of time-dependent sensor readings up to the cognitive impairment state marker matches the second set of time-dependent sensor readings, activate an alert indicator in the helmet, wherein the alert indicator is a physical device that warns the wearer of the helmet of an impending recurrence of an impaired cognitive state for the wearer of the helmet.

19. The computer system of claim 18, wherein the alert indicator advises the wearer of the helmet to take an action that has been predetermined to avoid receiving a second cognitive impairment state signal from the observer.

20. The computer system of claim 18, wherein the program instructions are provided as a service in a cloud environment.

* * * * *